United States Patent [19]

Gogins

[11] Patent Number: 5,203,201
[45] Date of Patent: Apr. 20, 1993

[54] ON-LINE WEB FILTRATION EFFICIENCY TEST METHOD

[75] Inventor: Mark A. Gogins, Roseville, Minn.

[73] Assignee: Donaldson Company, Inc., Minneapolis, Minn.

[21] Appl. No.: 810,836

[22] Filed: Dec. 20, 1991

[51] Int. Cl.$^5$ ............................................. G01N 15/08
[52] U.S. Cl. ............................................. 73/38; 73/37.7
[58] Field of Search ........................... 73/38, 37.7, 37.6

[56] References Cited

U.S. PATENT DOCUMENTS

| | | | |
|---|---|---|---|
| 4,311,037 | 1/1982 | Gotchel et al. | 73/38 |
| 4,382,378 | 5/1983 | Wadsworth et al. | 73/38 |
| 4,656,865 | 4/1987 | Callan | 73/38 |
| 4,676,092 | 6/1987 | Tuttle | 73/38 |
| 4,686,848 | 8/1987 | Casselberry et al. | 73/38 |
| 4,875,360 | 10/1989 | Ziemer | 73/38 X |
| 5,081,863 | 1/1992 | Reid | 73/38 |

FOREIGN PATENT DOCUMENTS 311145 12/1988 Japan ....................................... 73/38

Primary Examiner—Hezron E. Williams
Assistant Examiner—Joseph W. Roskos
Attorney, Agent, or Firm—Merchant, Gould, Smith, Edell, Welter & Schmidt

[57] ABSTRACT

An apparatus and method for measuring the filtration efficiency of a moving air-permeable web. The apparatus includes a sampling head with an upstream head and a downstream head disposed on opposite sides of the moving web and spaced apart to define a path for web travel. Particle laden air from the upstream head passes through the moving web and is collected in the downstream head where a sampling probe is disposed to collect filtered air for efficiency measurements. The method can be practice on-line in the media manufacturing process to continuously monitor the filtration characteristics and if necessary change the process condition to maintain the filtration characteristics within design parameters.

15 Claims, 4 Drawing Sheets

ON-LINE WEB FILTRATION EFFICIENCY TEST METHOD

BACKGROUND OF THE INVENTION

The present invention relates to an apparatus and process for measuring the filtration efficiency of a moving air-permeable web. It is particularly useful in the manufacture and processing of filter media.

In the prior art, the filtration efficiency of a media is done on stationary samples of the media after the manufacturing process is completed. If the media fails to meet design specifications, an entire lot of media from a particular manufacturing run may have to be discarded. The prior art has not provided for an on-line filtration efficiency test system whereby filtration performance can be measured continuously on a moving web as the media is being made or processed. There has been a need for such a system, because it would allow immediate corrective action and control of the media manufacturing process. The prior art test systems incorporate a sampling head that seals with the media. To use such an apparatus on-line would require that the moving web be stopped. This is not a viable solution to the problem of obtaining efficiency measurements on-line during the manufacturing process.

The present invention solves these problems associated with the prior art by providing a flow distributing and non-sealing sampling head positioned about the moving air-permeable web. It has been found that the present invention provides for accurate filtration efficiency measurements on the moving web during the manufacturing process, allowing for continuous monitoring of the web to ensure that the web being produced meets design specifications. If the filtration efficiency falls outside of the design specifications during the on-line testing, immediate corrective action can be taken.

SUMMARY OF THE INVENTION

The present invention is a method and apparatus for monitoring the filtration efficiency of an air-permeable web that includes a sampling head with first and second members that are disposed on opposite sides of the web, and spaced apart from the web. The apparatus has a means to introduce particle-laden air into the first sampling head member, which distributes the particle-laden air through the moving web. The second sampling head member collects the particle-laden air passing through the web. The apparatus further has a means to determine the efficiency of the removal of particles by the web. The sampling head members are spaced apart sufficiently such that as the moving head travels between them it will not contact either. In a preferred embodiment of the apparatus, the upstream sampling head has an air distribution outlet with a cross-sectional area that is greater than the cross-sectional area of the downstream head which collects the particle-laden air passed through the web. A sampling probe is disposed within the downstream head, and is positioned in the downstream head so that ambient air, that is air that has not passed through the web, is prevented from entering the sampling probe. The method of the present invention includes the steps of providing a sampling head with an upstream head and a downstream head having a sampling probe disposed on opposite sides of a moving web, and spaced apart to define a path for the web travel. The web is passed between the upstream head and downstream head and particle-laden air is distributed from the upstream head through the web and collected in the downstream head. Finally, the method of the present invention includes the step of determining the efficiency of the removal of particles from the air that has passed through the web.

As described above, the present invention provides for on-line and continuous monitoring of the filtration efficiency of a moving web of air-permeable media. This is particularly advantageous in that manufacturing processes ca be adjusted or modified on a real time basis if the measurements on the moving web fall outside of the desired design specifications. These, and other advantages of the present invention will become apparent with reference to the accompanying drawings, detailed description of the preferred embodiment, and claims.

DETAILED DESCRIPTION OF THE PREFERRED EMBODIMENT

Figure 1:
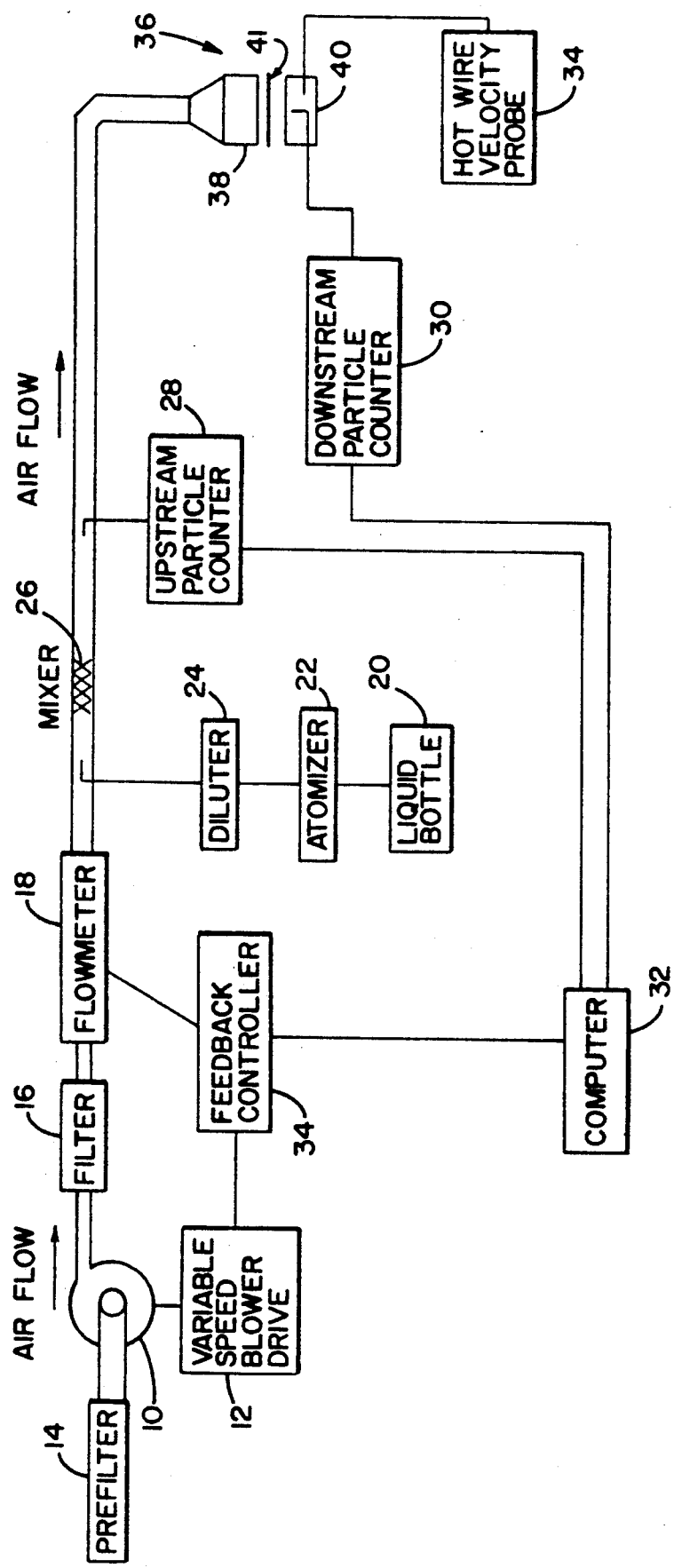
FIG. 1 is a block diagram illustration of the test method and apparatus of the present invention.

Referring to the drawings, wherein like numerals represent like parts throughout several views, FIG. 1 illustrates in functional block diagram form the components of the test apparatus of the present invention. With the exception of the sampling head which will be described in more detail below the elements shown in FIG. 1 are well-known in the prior art, and specifically, in test apparatus for measuring filtration efficiency of a stationary sample. These elements and the prior art test system in which they are used, are described in detail in a publication entitled "Design and Operation of Optimized High Efficiency Filter Element Test Systems", which was co-authored by the applicant herein, and presented in May of 1987 at the Annual Technical Meeting of the Institute of Environmental Sciences in San Jose, California. This publication is incorporated herein by reference.

In general, the test apparatus comprises a clean air source comprising a blower 10 with a variable speed drive 12, and a pre-filter 14. A filter 16, which may be a high-efficiency type (HEPA) is provided to further filter the air from blower 10. In addition, a flow meter 18 is provided to monitor the air speed. An aerosol source includes a liquid bottle or container 20, an atomizer 22 and diluter 24. A typical liquid aerosol material is oleic acid. Atomizer 22 provides a constant repeatable source of particles in a size range of interest. Using oleic acid as the test liquid, the aerosol as generated is typically a polydisperse with particle size in the ranges of 0.1 to 0.2 um. It should be understood that other liquids could be used in the aerosol source, and the atomizer 22 provides versatility and flexibility in that virtually any liquid can be sprayed from it to form a stable aerosol.

Diluter 24 is provided to reduce the concentration of the aerosol dispersion generated by atomizer 22. For example, the entire output of the atomizer may be used to test low penetration (less than $10^{-3}$) filters. For testing high penetration filters, the concentration of the aerosol must be reduced to avoid saturating the downstream particle counter.

The aerosol from the diluter is introduced into the airflow upstream of a static mixer 26 which functions to mix the aerosol with the primary air flow. The mixer is chosen and designed to provide thorough mixing of the aerosol in a manner that will not trap particles in recirculation zones, thus ensuring quick response time during testing.

The system is provided with an upstream particle counter 28, and a downstream particle counter 30, each of which is connected to computer 32. The particle counters may be laser particle counters (LPC), and are used to monitor upstream and downstream particle counts simultaneously. In a preferred embodiment, the particle counters are selected to be sensitive to particles from 0.1 um to about 2.0 um at a flow rate of 0.01 cubic feet per minute (CFM). Particle counters 28 and 30 must be sensitive to a wide range of particle sizes. Air velocity through the media to be tested is measured by a hot wire velocity probe 34, positioned downstream of the media, as will be described in more detail hereafter A feedback controller 34 regulates the speed of blower 10 through variable speed drive 12 in response to commands from computer 32 to maintain a constant volume flow rate.

The sampling head of the present invention is shown generally at 36. It includes an upstream head member 38, and a downstream head member 40. Head members 38 and 40 are spaced apart whereby a continuous web 42 of media travels therebetween, as will be described in more detail below.

It should be understood that the system just described, with the exception of the sampling head for the moving web is known in the prior art, and specifically corresponds to prior art test apparatus for measuring the filtration efficiency of stationary filter media. Sampling head 36 is shown in more detail diagrammatically, in FIG. 2. Upstream head member 38 has an air inlet 42, and an air distribution chamber 44. The sidewalls of sampling head 36 fan outwardly from air inlet 42 to an air distribution outlet 46. Thus, the cross-sectional area of chamber 44, taken as a cross-section through a central axis 48, of upstream head member 38, increases from inlet 32 to outlet 46. Disposed across chamber 44, in the path of airflow therethrough, is a perforated metal sheet or screen 50 which is located proximate outlet 46. In one embodiment screen 50 has holes of 1/16 inch diameter and the holes comprise approximately 23% of its area. Also positioned across outlet 46 is a honeycomb-like air flow straightener structure 52 defining a plurality of airflow channels, for example, at 54. Channels 54 are in one embodiment approximately $\frac{1}{8}$ inch in diameter and structure 52 is about one inch thick (measured along central axis 48). A second perforated metal screen may be placed across outlet 46 and in one embodiment has holes $\frac{1}{8}$ inch in diameter which comprise 40% of its surface area.

Downstream head member 40 is a housing defined by sidewalls as illustrated at 56 and air inlet 58 and air outlet 60. Disposed across air inlet 58 and air outlet 60 are honeycomb flow straightener structures 62 and 64 similar to structure 52 and as shown in more detail in FIG. 3. Structure 62 is at air inlet 58 of downstream head member 40, while structure 64 is at air outlet 60. Structures 62 and 64 define airflow channels for direction of airflow into downstream head 40 and out of downstream head 40, respectively. A downstream sample probe 66 is disposed within downstream head 40, and in a preferred embodiment, an inlet 68 of probe 66 is positioned at a central axis 70 of downstream head 40. In this preferred embodiment, upstream head member 38 and downstream head member 40, are positioned with their central axes 48 and 70 aligned.

Figure 2:
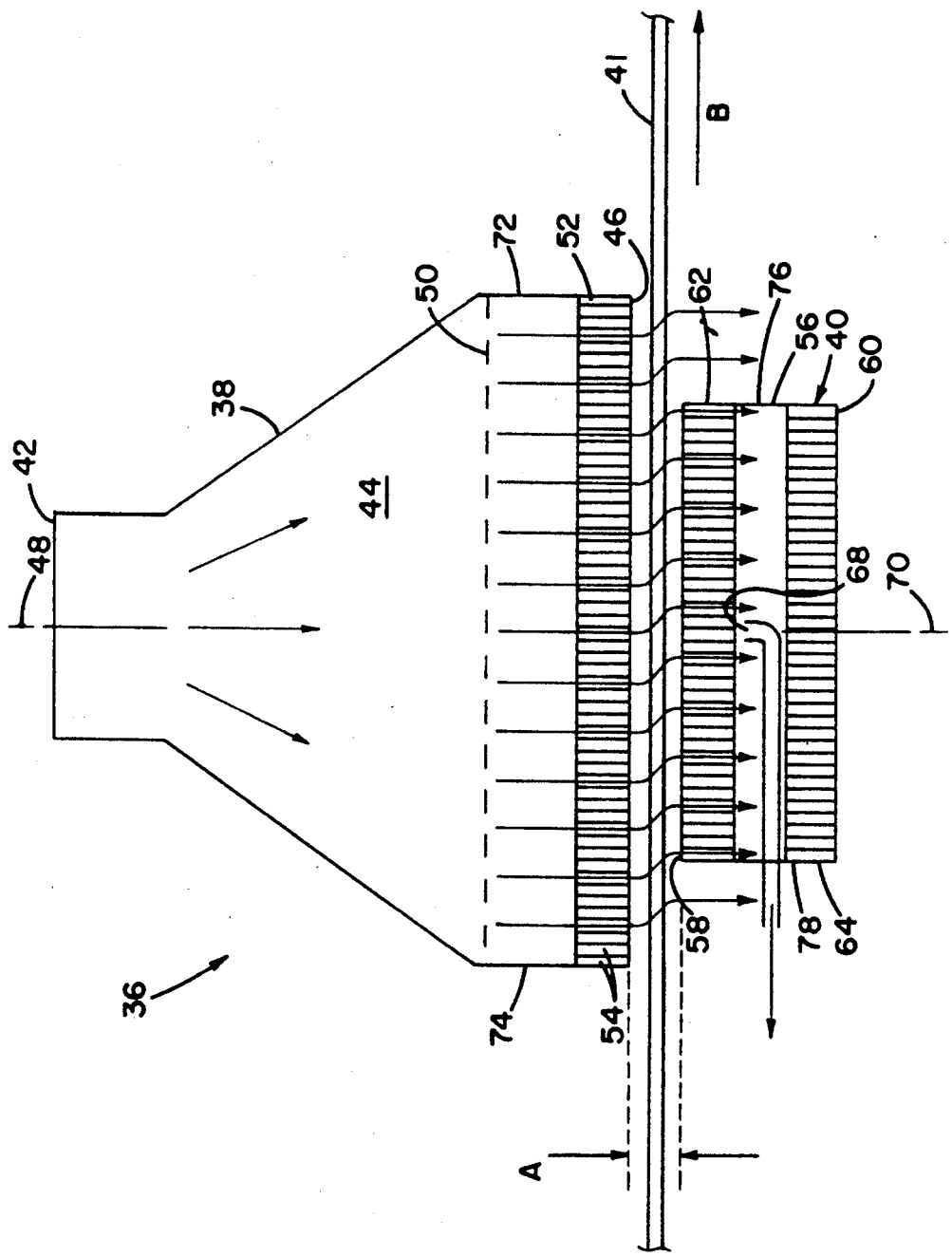
FIG. 2 is a schematic representation of the sampling head of the present invention shown in cross-section.
Figure 3:
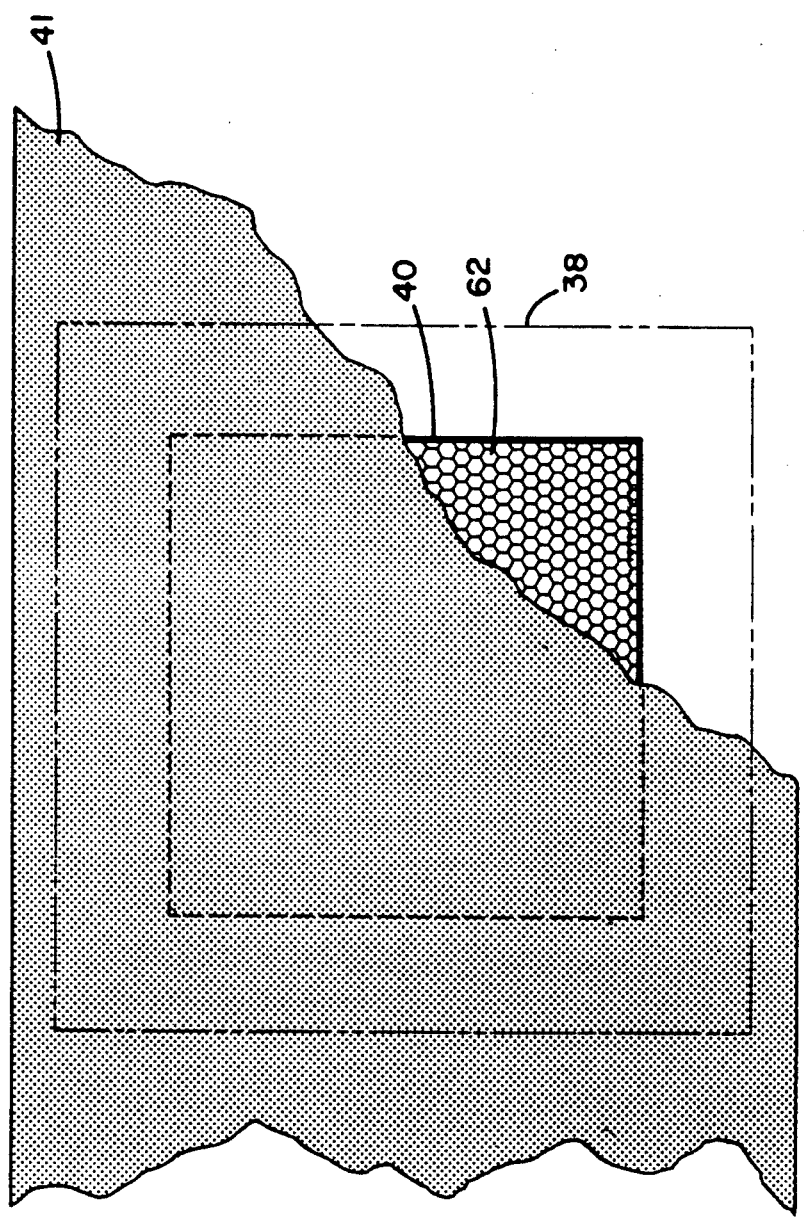
FIG. 3 is a plan view illustrating the positioning of the upstream and downstream heads of the present invention in relation to the web, portions of which are broken away for illustrative purposes.

As illustrated more specifically in FIG. 3, air distribution outlet 46 of upstream head member 38, which is shown in phantom lines in FIG. 3, has a larger cross-sectional area than air inlet 58 of downstream head 40. This overlap aids in purging ambient air from the media before it travels over the downstream head. Returning to FIG. 2, upstream head 38 and downstream head 40, are spaced apart a distance shown at A to provide a path of travel for a moving web 41. The separation A is selected to provide clearance between the web 41 and sampling head 36 as web 41 moves in a direction of travel as shown at the arrow designated B. Upstream head 38 has a leading end 72, and a trailing end 74, defined in relation to the direction B of web travel. Similarly, downstream head 40 has a leading end 76 and trailing end 78, also defined with relation to the direction B of web travel. Trailing end 78 of downstream 40 is spaced from trailing end 74 of upstream 38 in the direction B of web travel. This aids in excluding room or ambient air from entering downstream head 40. For example with web 41 moving at a high rate of speed ambient air tends to be drawn in the direction B of the web travel. By spacing trailing end 78 in the direction B from trailing end 74 air exiting upstream head 38 and through web 41 tends to blow ambient air away from inlet 58. Sample probe 66 is spaced from trailing end 78 of downstream head 40 also in the direction B of web travel to also insure that only filtered particle laden air, not ambient air, is collected by probe 66. As shown in FIG. 2, the air from upstream head 38 will be displaced in the direction B of web travel as it exits through distribution outlet 46, passes through media 41 and passes into downstream head 40. Downstream head 40 straightens the airflow in structure 62. It has been found that at web speeds in the range of 400 feet per minute the displacement of the particle-laden air passing through the web 41 is approximately one inch in the direction B of web travel. It can be seen that there will be leakage of some of the air exiting through air distribution outlet 46 from upstream head 38. Leakage will be in the area of overlap of air outlet 46 with the smaller air inlet 58 of downstream head 40. The airflow through the media has been found to be most vertical, i.e., straight through the media, at central axis 48 of upstream had 38. Thus, it is preferred to align probe inlet 68 centered along axis 48.

In the preferred test method, airflow through media 41 is selected to be approximately 20 CFM. Because of leakage, the total flow through upstream head 38 must be maintained at approximately 150 CFM. Variable speed blower 10 can be controlled to maintain a constant volume flow rate through upstream head 38. Alternatively, the air-speed detected by velocity probe 34 can be used to regulate variable speed blower drive 12 to maintain a constant velocity through media 41.

Figure 4:
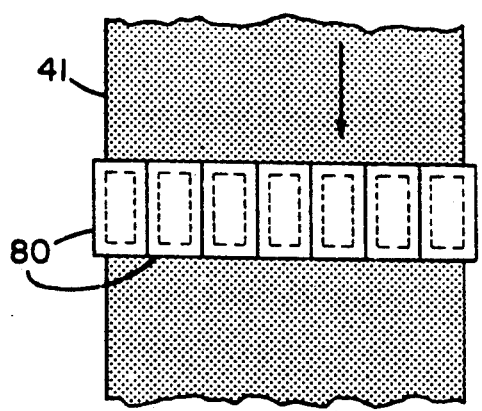
FIG. 4 illustrates an alternative embodiment of the present invention.
Figure 5:
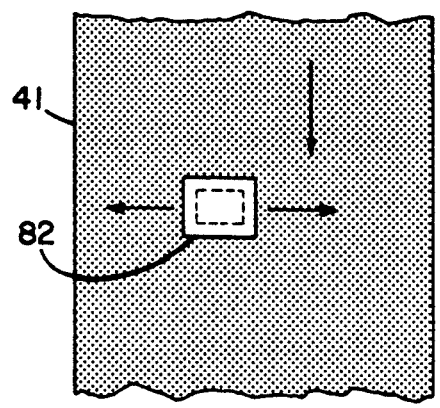
FIG. 5 is another alternative embodiment of the present invention.

In the embodiment illustrated in FIGS. 2 and 3, only one sampling head 36 is used and is shown as measuring efficiency through generally the central or middle portion of web 41. FIG. 4 illustrates an alternative embodiment, wherein a plurality of like sampling heads 80 are disposed across the width of web 41. Individually, each of sampling heads 80 has the structure previously described with respect to sampling head 38. Mounting of multiple sampling heads, as shown in FIG. 4 permits measuring uniformity of filtration characteristics of the web along the web and across the web. FIG. 5 illustrates another alternative embodiment where a sampling head 82 is mounted to traverse across the width of moving web 41. Sampling head 82 is also structured in the same manner as previously described with respect to sampling head 38. By mounting sampling head 82 for transverse movement across the web, the uniformity along the web and across the web can also be measured.

Figure 6:
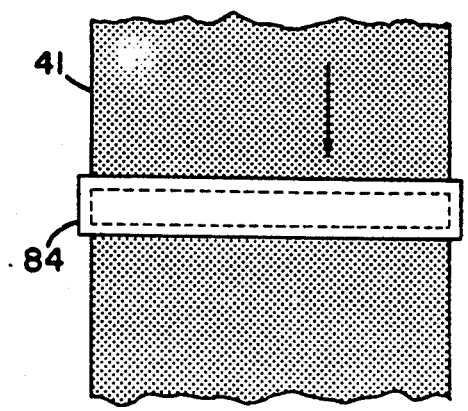
FIG. 6 is another alternative embodiment of the present invention.

FIG. 6 also illustrates another alternative embodiment of the present invention whereby a sampling head 84 is sized to be at least as wide as web 41. Sampling head 84 also allows for measurement of uniformity along the web, and average efficiency across the web.

The above-described on-line web filtration efficiency test system and method has been found to provide consistent results in continuously monitoring media efficiency during the manufacturing process. It can be used, for example, to monitor a particular process step. The on-line efficiency measurements can be taken by sampling heads positioned in the process line before and after a particular process step. In this manner, the process itself can be controlled on a substantially real time basis to ensure that the media being produced meets design specifications.

The apparatus and method of present invention is a significant improvement over the prior art which provided only for static or stationary testing of the media. The prior art did not provide for continuous and real time process and monitoring and control.

What is claimed is:

1. Apparatus for monitoring the filtration efficiency of an air permeable moving web comprising:
   a sampling head having first and second members disposed on opposite sides of the moving web, each spaced apart from the web and defining a path through which the web travels without contacting said first and second members;
   means for introducing particle laden air into said first member, said first member distributing the particle laden air through the web while the web is moving, said second member collecting the particle laden air passing through the moving web;
   means for determining the efficiency of the removal of particles from the air by the air permeable web.

2. A sampling head for use in a system for measuring the filtration efficiency of a moving web comprising:
   an upstream head adapted to distribute particle laden air through the web while the web is moving;
   a downstream head adapted to collect the particle laden air passed through the moving web;
   said upstream and downstream heads spaced apart from each other on opposite sides of the web to provide a path through which the moving web travels without contacting either of said heads whereby efficiency measurement is accomplished without a seal between either of said heads and the web.

3. A sampling head in accordance with claim 2 wherein said upstream head has an air distribution outlet of a first cross-sectional area and said downstream head has an air inlet of a second cross-sectional area smaller than said first cross-sectional area.

4. A sampling head in accordance with claim 3 wherein said upstream and downstream heads have central axes disposed perpendicular to the web and which are aligned with each other.

5. A sampling head in accordance with claim 2 wherein said upstream head has an air distribution outlet with a leading end and a trailing end, and said downstream head has an air inlet with a leading end and a trailing end, said trailing end of said air inlet spaced from said trailing end of said air distribution outlet in the direction of travel of the web.

6. A sampling head in accordance with claim 5 wherein said downstream head further comprises a sampling probe disposed therein, said sampling probe spaced from said trailing end of said downstream head in the direction of web travel.

7. A sampling head in accordance with claim 6 wherein said upstream head has a central axis perpendicular to the web and said sampling probe is aligned generally along said central axis.

8. A sampling head in accordance with claim 2, wherein said sampling head is mounted for transverse movement across the width of the moving web whereby the filtration efficiency of the moving web can be measured across its entire width.

9. A sampling head in accordance with claim 2, wherein said sampling head has a width at least as wide as the moving web.

10. A method of measuring the filtration efficiency of a moving web of air permeable material comprising the steps of:
    providing a sampling head comprising an upstream head and a downstream head having a sampling probe, said upstream head and downstream head disposed on opposite sides of the web and spaced apart from each other to define a path for the web travel;
    passing the web between the upstream head and downstream head without the web contacting either of said heads;
    distributing particle laden air from the upstream head through the web;
    collecting in the downstream head the air passing through the web;
    determining the efficiency of the removal of particles from the air passing through the web.

11. A method in accordance with claim 10, further comprising:
    the step of preventing ambient air from passing through the web into the sampling probe.

12. A method in accordance with claim 11 wherein the step of preventing ambient air from passing into the sampling probe further comprises:
    the step of positioning said downstream head along the direction of web travel with respect to said upstream head whereby only filtered particle laden air from the upstream head is sampled by the probe.

13. A method in accordance with claim 10, wherein the step of providing a sampling head comprises:
    the step of providing multiple sampling heads across the width of the moving web, each of the sampling heads comprising:
    an upstream head and a downstream head having a sampling probe, with the upstream head and downstream head positioned on opposite sides of the web and spaced apart from each other to define a path for the web travel.

14. A method in accordance with claim 10, further comprising the step of moving the sampling head transversely across the width of the moving web.

15. A method in accordance with claim 10, further comprising the step of measuring the filtration efficiency of a moving web before and after a process step.

* * * * *